(12) United States Patent
Lira

(10) Patent No.: US 6,762,341 B2
(45) Date of Patent: Jul. 13, 2004

(54) USES OF MAMMALIAN CCR8 RECEPTORS AND RELATED REAGENTS

(75) Inventor: Sergio A. Lira, Chatham, NJ (US)

(73) Assignee: Schering Corporation, Kenilworth, NJ (US)

( * ) Notice: Subject to any disclaimer, the term of this patent is extended or adjusted under 35 U.S.C. 154(b) by 310 days.

(21) Appl. No.: 09/780,724

(22) Filed: Feb. 9, 2001

(65) Prior Publication Data

US 2003/0148369 A1 Aug. 7, 2003

Related U.S. Application Data

(60) Provisional application No. 60/181,638, filed on Feb. 10, 2000.

(51) Int. Cl.[7] ........................ A01K 67/27; A01K 67/00; A01K 67/033
(52) U.S. Cl. ............................................. 800/18; 800/8
(58) Field of Search ....................................... 800/18, 8

(56) References Cited

FOREIGN PATENT DOCUMENTS

| WO | WO 99/06561 | 2/1999 | ........... C12N/15/12 |
|---|---|---|---|
| WO | WO 99/25734 | 5/1999 | ........... C07K/14/00 |

OTHER PUBLICATIONS

Mullins, 1996, J. Clin. Invest., vol. 98, pp. S37–S40.*
Lederman, 2000, Experimental Physiology, vol. 85, pp. 603–613.*
Campbell and Wilmut, 1997, Theriogenology, vol. 47, pp. 63–72.*
Leonard, 1995, Immunological Reviews, vol. 148, pp. 97–114.*
Griffiths, 1998, Microscopy Research and Technique, vol. 41, pp. 344–358.*
Capecchi, 1994, Scientific American, vol. 270, pp. 34–41.*
Capecchi, 1989, Trends in Genetics, vol. 5., pp. 70–76.*
Zingoni et. al., 1998, Journal of Immunology, vol. 161, pp. 547–551.*
Napolitano M. et al., "Structure and function of the CC chemokine receptor (CCR) 8", *Forum* (Genova) 9(4):315, XP001012929 (1999).
Luttichau H.R. et al., "A highly selective CC chemokine receptor (CCR) 8 antagonist encoded by the poxvirus molluscum contagiosum", *Journal of Experimental Medicine*, 191(1):171, XP001008530 (Jan. 3, 2000).
International Search Report for International Application No. PCT/US 01/04161 dated Aug. 17, 2001, from European Patent Office.

* cited by examiner

*Primary Examiner*—Peter Paras, Jr.
*Assistant Examiner*—Valarie Bertoglio
(74) *Attorney, Agent, or Firm*—Michael G. Biro; Immac J. Thampoe

(57) ABSTRACT

Compositions and methods for using mammalian CCR8 receptor proteins, antagonists and related reagents to treat diseases or conditions associated with Th2-mediated responses in an individual, especially asthma, are provided. The methods comprise administering a therapeutically effective amount of a CCR8 antagonist, alone or in combination with other therapeutic reagents. Also provided are methods for screening for therapeutics. Genetically-engineered animals and their use as models of molecular mechanism are also provided.

2 Claims, No Drawings

USES OF MAMMALIAN CCR8 RECEPTORS AND RELATED REAGENTS

The present application claims the benefit of U.S. Provisional Application No. 60/181,638 filed Feb. 10, 2000.

FIELD OF THE INVENTION

The present invention relates to methods for using proteins which function in controlling development, differentiation, trafficking, and physiology of mammalian cells, e.g., cells of a mammalian immune system. More particularly, it provides methods using proteins and mimetics which regulate cellular pulmonary inflammation and methods of treating diseases or conditions associated with Th2-mediated hypersensitivity states, such as asthma.

The present invention also relates to genetically engineered non-human animals and their use as molecular models in the study of the CCR8 chemokine receptor and molecules affected by the action of CCR8.

BACKGROUND OF THE INVENTION

The chemokines are a sub-family of chemoattractant cytokines that were classically characterized by their ability to mediate leukocyte trafficking by binding to specific G-protein linked seven transmembrane spanning receptors, or GPCRs [Baggiolini et al., 1998, Nature 392:565–568]. This activity, and the observance of chemokine production in diverse inflammatory settings, has implicated chemokines as mediators of immune and inflammatory responses [Sallusto et al., 1998, Immunol. Today 19:568–574; Moore et al., 1998, J Lab. Clin. Med. 132:97–103; Tabu et al., 1996, J. Immunol. 156:2095–2103]. Chemokine receptors transduce signals important for the development and trafficking of specific leukocyte subsets. [Rollins et al., 1997, Blood 90:909–928; Premack et al., 1996, Nat. Med. 2:1174–1178; Murphy et aL, 1994, Ann. Rev. Immunol. 12:593–633]. In order to help clarify the physiological function of the chemokines and their receptors, recent efforts have focused on defining the cellular expression and distribution of chemokine receptors. To date, several of these G-protein coupled receptors have been characterized and evidence suggests that they are differently expressed among leukocyte populations. [Mackay et al., 1996, J Exp. Med., 184:799–802; Locati et al., 1999, Ann. Rev. Med. Med. 50:425–440]. In particular, lymphocyte subpopulations are reported to display restricted expression of chemokine receptors, raising the possibility of receptor-based immune manipulation [Oppenheim et al., 1997, Clinical Cancer Research 3:2682–2686].

CCR8 is a chemokine receptor [WO 99/06561] whose expression is primarily restricted to Th2 cells [Zingoni et al., 1998, J Immunol. 161:547–551; D'Ambrosio et al., 1998, J Immunol. 161:5111–5115]. Indeed, the ligands for this receptor, I-309 in humans and TCA3 in mice, are chemotactic for Th2 cells in vitro [D'Ambrosio et al., 1998, J. Immunol. 161:5111–5115]. The viral chemokines vMIP-1, vMIP-II and vMCC-1 have also been reported to have high affinity to CCR8: vMIP-1 acts as a CCR8 agonist [Endres et al., 1999, Exp. Med. 189:1993–8; Sozzani et al., 1998, Blood 92:4036–39], while vMIP-II and vMCC-1 act as potent antagonists [Dairoghi et al, J. Biol Chem 294(31):21569–74]. However, the in vivo function of CCR8 and its ligands is yet unknown.

Medical science relies, in large degree, on appropriate recruitment or suppression of the immune system in effecting cures for insufficient or improper physiological responses to environmental factors. However, the lack of understanding of how the immune system is regulated or differentiates has blocked the ability to advantageously modulate the immunological mechanisms to biological challenges, i.e., response to biological injury. Medical conditions characterized by abnormal or inappropriate regulation of the development or physiology of relevant cells, such as asthma, thus remain unmanageable. The discovery and characterization of specific regulatory pathways and their physiological effects will contribute to the development of therapies for a broad range of degenerative or other conditions which affect the biological system, immune cells, as well as other cell types. Understanding the role of immune cells and their overall finction in the development of various inflammatory conditions has been hampered by the lack of in vivo models. The present invention provides solutions to some of these and many other problems.

SUMMARY OF THE INVENTION

The present invention is based, in part, upon the discovery of the physiological role of the chemokine receptor CCR8 in various models of immune response. In particular, the role of CCR8 has been elucidated in pathways involved in Th2-mediated allergic responses, particularly asthma. This invention, therefore, provides methods of treating allergic or other diseases using agonists and antagonists of CCR8, as well as methods for screening for drugs useful in such treatment using CCR8 as a screening target. The invention also relates to the identification of a model system to study the role and function of CCR8 receptors through the use of genetically engineered animals which lack a functional CCR8 gene.

The present invention provides methods for treating a Th2-mediated condition in an animal, the methods comprising administering to the animal a therapeutic amount of an antagonist of a mammalian CCR8 receptor. Specifically, the invention provides methods for treating asthma in an animal comprising administering an antagonist of a mammalian CCR8 receptor. Preferred embodiments include where the antagonist is an antibody which binds to the mammalian CCR8 receptor, or where the antagonist is a small molecule inhibitor. Further embodiments include where the antagonist is a modified chemokine ligand. The administering may be in combination with: an anti-inflammatory agent; a cytokine agonist or antagonist including especially an antagonist of a Th2 cytokine such as IL-5, IL-13 or IL-4; an analgesic; a steroid or an antihistamine.

Also provided by the present invention are methods of screening for drugs useful for treating diseases associated with the immune response such as asthma. In a preferred embodiment, CCR8 is used as a target to screen for asthma therapeutics.

The invention also provides a genetically engineered non-human animal whose genome lacks a functional CCR8 gene, and methods for its use as a model for molecular mechanism.

DETAILED DESCRIPTION OF THE PREFERRED EMBODIMENTS

I. General

The human and murine CCR8 receptors are homologous G-protein coupled receptors, which were previously known under the names Terl [Napolitano, et al. (1996) J. Immunol. 157:2759–2763], ChemR1 [Samson, et al. (1996) Genomics 36:522–526], or CKR-L1 [Zabellos, et al. (1996) Biochem. Biophys. Res. Commun. 227:846–853]. See GenBank accession numbers AF005210 (partial) and U45983; WO 99/06561. The terms "CCR8", "CCR8 receptor" and "CCR8 receptor polypeptide" as used hereinafter refer to the receptor polypeptides described therein, as well as physical and functional variants, including species and allelic variants, and fragments thereof. The invention relates not only to peptides and peptide derivatives of naturally occurring CCR8, but also to CCR8 mutants and chemically synthesized derivatives of CCR8 that maintain CCR8 activity. For example, changes in the amino acid sequence of CCR8 are contemplated in the present invention. CCR8 can be altered by changing the DNA encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine to methionine; serine to threonine; threonine to serine; tryptophan to tyrosine; tyrosine to tryptophan or phenylalanine; valine to isoleucine or leucine. Additionally, other variants and fragments of CCR8 can be used in the present invention. Variants useful for the present invention comprise analogs, homologs, muteins and mimetics of CCR8 that retain the activity of naturally occurring CCR8. Peptides of CCR8 refer to portions of the amino acid sequence of CCR8 that also retain this activity. The variants can be generated directly from CCR8 itself by chemical modification, by proteolytic enzyme digestion, or by combinations thereof. Additionally, genetic engineering techniques, as well as methods of synthesizing polypeptides directly from amino acid residues, can be employed.

The ligands for the human CCR8 chemokine receptor have been identified as the I-309 protein [Roos, et al. (1997) *J. Biol. Chem.* 272:17251–17254; Tiffany, et al. (1997) *J. Exp. Med.* 186:165–170; GenBank Accession Numbers M57502 and M57506], TARC and MIP-1β [Bernardini et al., 1998, *J. Immunol.* 28:582–588; Sozzani et al., 1998, *Blood* 92:4036–4039]. The mouse ligand is identified as TCA-3 [GenBank Accession Numbers M17957 and X52401; Goya et al., 1998, *Immunol* 160:1975–1981]. The viral chemokines vMIP-I, vMIP-II, and vMCC-1 have also been reported to have high affmity to CCR8; vMIP-1 acts as a CCR8 agonist [Endres et al., 1999, *J. Exp. Med.* 189:1993–8; Sozzani et al., 1998, *Blood* 92:4036–39], while vMIP-II and vMCC-I act as potent antagonists [Dairaghi et al., 1999, *J Biol. Chem.* 274631:21569–740].

CCR8 has recently been characterized as being preferentially expressed on Th2 cells [Zingoni et al., 1998, *Cells J. Immunol* 161:547–551; D'Ambrosio et al., 1998, *J. Immunol* 161:5111–5115; PCT/US98/23240]. Additionally, the natural human CCR8 ligand has been shown to attract Th2-polarized T cells in vitro with considerable vigor [Zingoni et al., 1998, *J. Immunol.* 161:547–51]. To study the biological role of CCR8 in vivo, a CCR8 deficient (–/–) knockout mouse (KO) was generated. The KO mice were tested in a number of established models of pulmonary inflammation: (a) models of type 1 and type 2 pulmonary granulomatous inflammation; (b) two models of allergic airway inflammation that recapitulate many aspects of human asthma. The results of these experiments surprisingly suggest that CCR8 may have a key role in the allergic response and may constitute a novel therapeutic target for asthma.

A. *S. Mansoni* Egg & *M. Bovis* PPD Antigen Models

In order to define the specific participation of CCR8 in Th1- and Th2-mediated immune responses in vivo, the CCR8 KO mice were first tested in well described models of type 1 and type 2 pulmonary granulomatous inflammation elicited by antigens derived from Mycobacteria bovis and ova of the helminth parasite, Schistosoma manson [Chensue et al., 1994, *Am. J Pathol.* 145:1105–1113; Chensue et al., 1995, *J Immunol* 154:5969–5976]. The Th2 dependency of the secondary schistosome egg-induced granuloma is well established [Wynn et al., 1995, *Curr. Opin. Immunol* 7:505–511]; IL-4, IL-5 and IL-13 all contribute to the response [Sher et al., 1990, *Proc. NatL. Acad. Sci. USA* 87:61–65; Cheever et al., 1994, *J. Immunol* 153:753–759; Chiaramonte et al., 1999, *J. Immunol* 162:920–930]. It was surprisingly discovered that Th2 responses induced by *Schistosoma mansoni* soluble egg antigens are defective in the CCR8 –/– mice. The primary response to *S. mansoni* eggs was characterized by decreased IL-5 and IL-13 production and abrogated granuloma formation (Example V). The secondary response to schistosome antigens likewise showed impaired IL-5 and IL-13 production that was associated with aberrant type-2 granulomas displaying a 50% reduction in eosinophil content (Example VI). The reduction in eosinophil numbers in the granulomas was associated with reduced eosinophil production by the bone marrow and systemic reduction of IL-5 (Example VIII). In contrast, a prototypical Th1 immune response, elicited by *Mycobacteria bovis* purified protein derivative (PPD), is unaffected in CCR8 –/– mice (Example VII).

These studies thus revealed impaired Th2 cytokine production and eosinophil recruitment during the type-2 response, with no abrogation of the type-1 response. Since normal circulating eosinophils were unresponsive to CCR8 ligands, their impaired mobilization was attributed to the abrogation of Th2 cytokines rather than a direct eosinophil chemotactic defect (Example IX). These findings suggest that CCR8 is required for normal Th2 cell function, maturation or mobilization. Thus, CCR8 may provide a potential target for selective therapeutic manipulation of Th-2 mediated hypersensitivity states.

B. Cockroach Antigen Model

One Th2-mediated disease which is acquiring epidemic proportions is asthma. Lymphocytes and eosinophils have been identified as populations that correlate to the intensity and severity of the asthmatic response [Boyce et al., 1997, *Chest* 112: 1234–40; Umetsu et al., 1997, *Proc. Soc. Exp. Biol. Med.* 215:11–20]. The production of specific Th2 cytokines, such as IL-5, have clearly been shown to allow eosinophils to mature, be released and maintained in the peripheral circulatory system. To test whether CCR8 is important in this response, the CCR8 –/– mice were tested in the cockroach allergen model of asthma. [Campbell et al., 1998, *J. Immunol* 161:7047–53; de Blay et al., 1997, *J. Allergy Clin Immunol* 163:2160–67; Jaen et al., 1997, *Engl J Med* 337:791–2; Kuster et al., 1996, *Pediatr Nurs* 22:297–303; J. Roberts, 1996, *BMJ* 312:1630; Rosenstreich et al., 1997, *N Engl J Med* 336:1356–63; Sarpong et al., 1996, *J. Clin Immunol* 97:1393–401; F. A. Schulaner, 1997, *N Engl J Med* 337:791; discussion 792 (1997)].

Only a slight, nonsignificant difference in T lymphocyte numbers was found between allergic control and CCR8–/– mice (Example X). Histological analysis revealed an increase in the number of mononuclear phagocytes and a significant reduction in granulocyte numbers (eosinophils) in the CCR8–/–mice (Example XII). In addition, a significant reduction was found in eosinophil peroxidase levels (EPO) in the BAL fluid of the CCR8 −/− animals, confirming a lower level of eosinophil participation in the response. There was no difference in the numbers of eosinophils between non-challenged +/+ and −/− CCR8 mice. In contrast, there was a significant reduction in the numbers of circulating eosinophils in the antigen-challenged mice. These results suggest a deficit in eosinophil maturation and release into circulation.

The role of IL-5 in mediating eosinophil maturation, release from the bone marrow and migration toward specific chemoattractants expressed in inflamed tissue [Clutterbuck et al., 1997, Blood 73:1504–12; Ohkawara, et al., 1997, *Am. J Respir Cell Mol Biol* 16:510–20; Yousefi et al., 1997, *Int Arch Allergy Immunol* 112:9–12] makes its regulation of potential great importance in the pathophysiology of several diseases, especially asthma [Sur et al., 1996, J Allergy Clin Immunol 97:1272–8; Collins et al., 1995, J Exp Med 182:1169–74]. A significant decrease in IL-5 levels was observed in the lungs of CCR8 −/− allergic mice (Example XII). This decrease correlated directly with the deficit of circulating and accumulated eosinophils in the CCR8 −/− mice.

Levels of IFN-γ, IL-10, and IL-12 were not altered within the CCR8 −/− samples compared to the littermate control lungs (Example XIII). However, the levels of pulmonary IL-4 and IL-13 were significantly reduced in the CCR8−/− mice compared to the littermate control mice during the developing stages of disease after an allergen challenge. Interestingly, IL-4 levels were reduced early, whereas IL-13 levels were significantly altered during the latter stages of the disease. These findings, along with the IL-5 data above, indicate a defective Th2 response in these animals.

A hallmark of Th2 allergic responses is increased levels of serum IgE [Erger et al., 1997, *Ann. Allergy Asthma Immunol* 78:566–8; Yssel et al., 1998, *Clin. Exp. Allergy* Suppl 5:104–9; discussion 117–8; J. P. Kinet, 1999, *Ann. Rev Immunol.* 17:931–72; H. L. Spiegelberg, 1984, *Adv. Immunol.* 35:61–88]. Chronically sensitized CCR8 −/− mice demonstrated a significant decrease in total circulating levels of IgE as compared to challenged littermate control mice (Example XIV). These results indicate that deletion of CCR8 may drastically alter the sensitization process in this model and suggest that CCR8 deletion may negatively influence the overall Th2 type response.

Reduced levels of regulatory cytokines could potentially affect production of eosinophil chemoattractant molecules. Both IL-4 and IL-13, for instance, have been shown to regulate production of eotaxin and other eosinophil chemoattractant molecules in the airways [Mochizuki et aL, 1998, *J Immunol* 160: 60–8; O'Hehir et al., 1996, *Clin Exp Allergy* 26:20–7; Li et al., 1999, *Immunol* 162(5):2477–87; Teran, et al., 1999, *Am. J Respir Cell Mol Biol* 20:777–86; Shinkai et al., 1999, *J Immunol* 163:1602–10; Hogaboam et al., 1999, *J Immunol* 162: 6071–9]. Therefore, several eosinophil associated chemokines, including C10, eotaxin, RANTES, MIP-1 alpha, and MCP-3, were measured (Example XIV). The levels of these chemokines within the lung parenchyma were similar between challenged CCR8+/+ and −/− mice. The only exception was eotaxin, which was shown to be significantly reduced in the CCR8−/− mice. Eotaxin is a potent eosinophil chemoattractant in vitro and in vivo, and a reduction in its production during the allergic response could contribute to the reduced eosinophil recruitment observed here [Lamkhioued et al., 1997, *J Immunol* 159:4593–601; Rothenberg et al., 1996, *Mol Med* 2:334–48; Jose et al., 1994, *J Exp Med* 179: 881–7]. These results demonstrate that a deficit in CCR8can induce a disregulation in both cytokine and chemokine networks, resulting in significant deficit in the ability to mobilize eosinophils into the lung parenchyma.

Changes in airway physiology were also assessed in sensitized mice during development of the allergic airway responses after allergen rechallenges (Example XV). After a single intratracheal allergen challenge, the CCR8−/− mice showed no alteration in airway hyperreactivity. However, the pathophysiological responses associated with severe asthma are associated with multiple exposures, therefore making chronic asthmatic responses most relevant. Therefore, we examined whether deletion of CCR8affected the pathophysiologic responses to methacholine in a more chronic setting. After a second intratracheal allergen challenge, given 48 hours post-primary challenge, the CCR8−/− mice demonstrated a significantly attenuated airway hyperactive response. These results indicate that CCR8is important in the development of airway hyperreactivity after chronic allergen challenges. Previous studies using this model have indicated that the secondary challenge stage (chronic stage) directly correlates with the intensity of eosinophil accumulation and activation [Campbell et al., 1998, *J Immunol* 161:7047–53]. Thus, these results relate directly with the above data indicating decreased eosinophil accumulation and activation.

C. Ovalbumin Model

To establish that the reduction of antigen-induced pulmonary eosinophilia in CCR8−/− mice is not specific to the cockroach antigen, mice were sensitized and challenged with ovalbumin (Example XVI). After sensitization and challenge with ovalbumin, CCR8−/− mice had fewer eosinophils in the bronchoalveolar lavage fluid ($39\pm7\times10^3$ eosinophils/ml) compared to those found in the bronchoalveolar lavage fluid of ovalbumin challenged wild type controls ($398\pm108\times10^3$ eosinophils/ml). These results were confirmed by histological analysis of the peribronchial regions of the lungs (Example XVII) where a 70% reduction in the number of peribronchial eosinophils were found in sensitized, ovalbumin challenged CCR8−/− mice relative to values in wild type controls (CCR8+/+). These results indicate that the reduction in antigen-induced pulmonary eosinophilia in CCR8−/− mice is not specific to the cockroach antigen and the CCR8serves an important role in the induction of pulmonary eosinophilia.

Taken together, our results show that CCR8plays an important role in Th2 cell function in vivo and provide support to the concept that chemokines and their receptors could be targeted to modulate specific types of T cell-mediated immune responses.

In the *S. mansoni* egg model, IL-4, IL-5 and IL-13 all contribute to the Th2 response. In CCR8−/− mice, IL-4, IL-5 and IL-13 were reduced in lymph node cultures. Likewise, in granulomatous lungs, IL-5 and IL-13 were abrogated, however IL-4 was unchanged, although transcripts and protein levels were very low in both control and knockout mice. The failure to observe IL-4 changes in the lung may have been due to compensation by other cell types. It is known that IL-4 can also be produced by double negative (CD4−CD8−) T cells, CD8+ type 2 T cells, and non-T and non-B cells [Cerwenka et al., 1998,*J Immunol.* 161:97–105; Cheever et al., 1994, *J Immunol.* 153:753–9; Cheng et al., 1996, *J Immunol.* 156:3591–601]. These cells may have contributed to the bulk of IL-4 seen in granulomatous lungs. Interestingly, in the cockroach antigen-induced asthma model, CCR8−/− mice display impaired IL-4 production in lungs within the first hours after challenge. Under these conditions, compensatory IL-4 producing cells may not yet be mobilized.

Interestingly, CCR8−/− mice are remarkably similar to IL-4 −/− mice in their response to schistosome egg antigens [Chensue et al., 1997, *J Immunol.* 159:3565–73]. In the type-2 response, both strains have reduced numbers of eosinophils in blood and granulomas associated with reduced levels of Th2-related cytokines. Both strains display increased IFN-γ production in lymph nodes following challenge with either mycobacterial or schistosomal antigens. Finally, the secondary type-2 granulomas seen in both IL-4 −/− and CCR8−/− mice did not completely shift to a type-1 profile, but rather established a compensatory Th2-like granuloma of similar size. Not surprisingly, CCR8−/− mice also share features of IL-5 −/− and IL-13 −/− mice [Brunet et al., 1999, *Infect. Immun.* 67:3014–8; McKenzie et al., 1998, *Immunity* 9:423–35] since as in IL-4 −/− mice both of these important effector cytokines were reduced by CCR8gene disruption. Thus, CCR8deletion results in a state most resembling IL-4 deficiency suggesting that CCR8ligation may be as important as IL-4 in determining Th2 effector finction.

Manipulation of the CCR8interaction can thus have important clinical implications. The role of CCR8in cytokine production and eosinophil accumulation suggests that CCR8is an important novel target in Th2-mediated hypersensitivity states such as asthma. Thus, in situations like asthma where CCR8signaling should be suppressed, a CCR8antagonist would be useful. Conversely, in settings where enhanced Th2 response is desired, agonists of CCR8could be used.

The CCR8KO mice of the present invention can now be used in studies of allergy, general immunity, viral immunity, and autoimmune diseases. Examples of other models which can be used to explore the role of CCR8include those described in Swanson et al., 1985, *J Allergy & Clin. Immunology* 76(5):724–29; Stevens et al., 1999, *J Immunol.* 162(12):7501–9; and Kung et al., 1994, *International Archives of Allergy & Immunol.* 105:83–90.

The descriptions below are directed, for exemplary purposes, to primate, e.g., a human, or rodent, e.g., mouse or rat CCR8and its ligands, but are likewise applicable to related embodiments from other species. Thus, conditions known to be mediated by or related to a Th2 response may be regulatable using these reagents.

II. Nucleic Acids

General description of nucleic acids, their manipulation, and their uses (including, e.g., complementary and antisense nucleic acids) are provided in the following references: McCaughein et al., "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (ed. 1987) *Teratocarcinomas and Embryonic Stem Cells: A Practical Approach* IRL Press, Oxford; Rosenberg (1992) *J. Clinical Oncology* 10:180–199; Cournoyer and Caskey (1993) *Ann. Rev. Immunol.* 11:297–329; Wetmur and Davidson (1968) *J. Mol. Biol.* 31:349–370; Weintraub (1990) *Scientific American* 262:40–46; Jaroszewski and Cohen (1991) *Advanced Drug Delivery Reviews* 6:235–250; Akhtar, et al. (1992) pages 133–145 in Erickson and Izant (eds.) *Gene Regulation: Biology of Antisense RNA and DNA* Raven Press, New York; Zhao, et al. (1994) *Blood* 84:3660–3666; Misquitta, et al. (1999) *Proc. Nat'l Acad. Sci. USA* 96:1451–1456; and Treco WO96/29411, each of which is incorporated by reference. Additional aspects will be apparent to a person having ordinary skill in the art in light of the teachings provided herein.

III. Purified CCR8

General descriptions of proteins and polypeptides in pharmaceutical or biochemical contexts can be found, e.g., in: Goodman, et al. (eds. 1990) *Goodman & Gilman's: The Pharmacological Bases of Therapeutics* (8th ed.) Pergamon Press; Avis, et al. (eds. 1993) *Pharmaceutical Dosage Forms: Parenteral Medications* Dekker, New York; Lieberman, et al. (eds. 1990) *Pharmaceutical Dosage Forms: Tablets* Dekker, New York; Lieberman, et al. (eds. 1990) *Pharmaceutical Dosage Forms: Disperse Systems* Dekker, New York; Freifelder (1982) *Physical Biochemistry* (2d ed.) W. H. Freeman; Cantor and Schimmel (1980) *Biophysical Chemistry*, parts 1–3, W.H. Freeman & Co., San Francisco. Specific descriptions of CCR8and its ligands are found, e.g., in WO99/25734. Recombinant methods for making the proteins are well known. Preparation of fragments by synthetic methods, or by biochemical cleavage of natural or recombinant forms, are also known to a person having ordinary skill in the art.

IV. Making CCR8

DNA which encodes CCR8, or ligands or fragments thereof, can be obtained by chemical synthesis, screening cDNA libraries, or by screening genomic libraries prepared from a wide variety of cell lines or tissue samples.

This DNA can be expressed in a wide variety of expression systems as described in, e.g.,WO 95/18826; Kaufmnan, et al. (1985) *Molec. and Cell. Biol.* 5:1750–1759; Pouwels, et al. (1985 and Supplements) *Cloning Vectors: A Laboratory Manual*, Elsevier, N.Y., Rodriguez, et al. (eds. 1988) *Vectors: A Survey of Molecular Cloning Vectors and Their Uses*, Buttersworth, Boston, Mass.; Rodriguez and Denhardt (eds.) *Vectors: A Survey of Molecular Cloning Vectors and Their Uses*, Buttersworth, Boston, Chapter 10, pp. 205–236; Okayama, et al. (1985) *Mol. Cell Biol.* 5:1136–1142; pMClneo Poly-A, see Thomas, et al. (1987) *Cell* 51:503–512; O'Reilly, et al. (1992) *Baculovirus Expression Vectors: A Laboratory Manual* Freeman and Co., CRC Press, Boca Raton, Fla.; Low (1989) *Biochem. Biophys. Acta* 988:427–454; Tse, et al. (1985) *Science* 230:1003–1008; and Brunner, et al. (1991) *J. Cell Biol.* 114:1275–1283; each of which is incorporated herein by reference.

Now that CCR8and its ligands have been characterized, fusion polypeptides, fragments, or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York; Bodanszky (1984) *The Principles of Peptide Synthesis* Springer-Verlag, New York; and Merrifield, et al. (1963) in *J. Am. Chem. Soc.* 85:2149–2156; each of which is incorporated herein by reference. Additional aspects will be apparent to a person having ordinary skill in the art in light of the teachings provided herein.

V. Physical Variants

Proteins or peptides having substantial amino acid sequence homology with the amino acid sequence of CCR8or its ligands are also contemplated. The variants include species or allelic variants. Homology, or sequence identity, is defined in, e.g.,WO 95/18826; Needleham, et al. (1970) *J. Mol. Biol.* 48:443–453; Sankoff, et al. (1983) Chapter One in *Time Warps. String Edits, and Macromolecules: The Theory and Practice of Sequence Comparison* Addison-Wesley, Reading, Mass.; software packages from NCBI, NIH; and the University of Wisconsin Genetics Computer Group, Madison, Wis.

The isolated DNA encoding CCR8or its ligands can be readily modified as described in, e.g., Sambrook, et al.

(1989); Ausubel, et al. (1987 and Supplements); Cunningham, et al. (1989) *Science* 243:1330–1336; O'Dowd, et al. (1988) *J. Biol. Chem.* 263:15985–15992; and Carruthers (1981) *Tetra. Letts.* 22:1859–1862; each of which is incorporated herein by reference. Additional methods will be apparent to a person having ordinary skill in the art in light of the teachings provided herein.

VI. Functional Variants

The blocking of the physiological interaction between CCR8and its ligands may result from the inhibition of binding of the ligand to the receptor by a variant of the natural ligand or antibody to the ligand, or by a variant of natural CCR8or antibody to CCR8. Methods for making such a variant are described in, e.g., Godowski, et al. (1988) *Science* 241:812–816; Beaucage and Carruthers (1981) *Tetra. Letts.* 22:1859–1862; Sambrook, et al. (1989) *Molecular Cloning: A Laboratory Manual* (2d ed.) Vols. 1–3, Cold Spring Harbor Laboratory; Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach*, IRL Press, Oxford; Cunningham, et al. (1989) *Science* 243:1339–1336; O'Dowd, et al. (1988) *J. Biol. Chem.* 263:15985–15992; and Lechleiter, et al. (1990) *EMBO J.* 9:4381–4390; each of which is incorporated herein by reference. Additional methods will be apparent to a person having ordinary skill in the art in light of the teachings provided herein.

VII. Specific Binding Compositions

A. Antibodies

The present invention provides for the use of an antibody or binding composition which specifically binds to CCR8, preferably a mammalian CCR8, e.g., primate, human, cat, dog, rat, or mouse. Antibodies can be raised to various CCR8proteins, including individual, polymorphic, allelic, strain, or species variants, and fragments thereof, either in their naturally occurring (full-length) forms or in their recombinant forms. Additionally, antibodies can be raised to these proteins in both their native (or active) forms or in their inactive, e.g., denatured, forms. Anti-idiotypic antibodies may also be used.

A number of immunogens may be selected to produce antibodies specifically reactive, or selective for binding, with CCR8proteins. Recombinant protein is a preferred immunogen for the production of monoclonal or polyclonal antibodies. Naturally occurring protein, from appropriate sources, e.g., primate, rodent, etc., may also be used either in pure or impure form. Synthetic peptides, made using the protein sequences described herein, may also be used as an immunogen for the production of antibodies to the proteins. Recombinant protein can be expressed and purified in eukaryotic or prokaryotic cells as described, e.g., in Coligan, et al. (eds.) (1995 and periodic supplements) *Current Protocols in Protein Science* John Wiley & Sons, New York, N.Y.; and Ausubel, et al (eds.) (1987 and periodic supplements) *Current Protocols in Molecular Biology*, Greene/Wiley, New York, N.Y. Naturally folded or denatured material can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the protein or peptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane *Antibodies, A Laboratory Manual*; or Coligan (ed.) *Current Protocols in Immunology*. Immunization can also be performed through other methods, e.g., DNA vector immunization. See, e.g., Wang, et al. (1997) *Virology* 228:278–284.

Monoclonal antibodies may be obtained by various techniques familiar to those skilled in the art. Typically, spleen cells from an animal immunized with a desired antigen are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies or binding compositions, including binding fragments and single chain versions, against predetermined fragments of CCR8proteins can be raised by immunization of animals with conjugates of the fragments with carrier proteins as described above. Monoclonal antibodies are prepared from cells secreting the desired antibody. These antibodies can be screened for binding to normal or defective CCR8protein. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.)

Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemilluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156.

Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

B. Other Molecules

Antibodies are merely one form of specific binding compositions. Other binding compositions, which will often have similar uses, include molecules that bind with specificity to a CCR8receptor or its ligand, e.g., in a binding partner-binding partner fashion, an antibody-antigen interaction, or in a natural physiologically relevant protein-protein interaction, either covalent or non-covalent, e.g., proteins which specifically associate with a CCR8protein. The molecule may be a polymer, or chemical reagent. A functional analog may be a protein with structural modifications, or may be a structurally unrelated molecule, e.g., which has a molecular shape which interacts with the appropriate binding determinants.

Drug screening using antibodies or CCR8or fragments thereof can be performed to identify compounds which have binding affinity to CCR8, or which can block the natural interaction with ligand. Subsequent biological assays can then be utilized to determine if the compound has intrinsic blocking activity and is therefore an antagonist. Likewise, a compound having intrinsic stimulating activity can signal to the cells via the CCR8and is thus an agonist in that it simulates the activity of a ligand.

As indicated above, known ligands for the CCR8chemokine receptor include I-309, TARC, MIP-1β, TCA-3, and the viral chemokine vMIP-I. Known chemokine ligand antagonists include the viral chemokines vMIP-II and vMCC-I. Mutein antagonists may be developed which maintain receptor binding but lack signaling. Structural studies of the ligand will also lead to design of new variants, particularly analogs exhibiting agonist or antagonist properties on the receptor. This can be combined with known screening methods to isolate muteins exhibiting desired spectra of activities.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. See, e.g., Meetings on High Throughput Screening, International Business Communications, Southborough, Mass. 01772–1749. Such molecules may compete with natural ligands, and selectively bind to the CCR8. Such specific binding compounds may be labeled or conjugated to toxic reagents.

VIII. Uses

Mammalian CCR8reagents will have a variety of therapeutic uses for, e.g., the treatment of conditions or diseases in which aberrant Th2 cell function and eosinophil recruitment has been implicated. These would include, e.g., mucosal inflammation of the gut or lung, including conditions such as allergy and asthma. In particular, the CCR8antagonists are useful as asthma therapeutics, and other CCR8reagents are useful for the identification and development of therapeutics for treating asthma.

Preferably, an administration regimen maximizes the amount of agonist or antagonist delivered to the patient consistent with an acceptable level of side effects. Accordingly, the amount of agonist or antagonist delivered depends in part on the particular agonist or antagonist and the severity of the condition being treated. Guidance in selecting appropriate doses is found in the literature on therapeutic uses of antibodies, e.g. Bach et al., chapter 22, in Ferrone et al., (eds.) (1985), *Handbook of Monoclonal Antibodies* Noges Publications, Park Ridge, N.J.; and Russell, pgs. 303–357, and Smith et al., pgs. 365–389, in Haber, et al. (eds.) (1977) *Antibodies in Human Diagnosis and Therapy*, Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Preferably, the CCR8antibody or binding composition thereof that will be used is derived from the same species as the animal targeted for treatment, thereby minimizing a humoral response to the reagent.

The total weekly dose ranges for antibodies or fragments thereof which specifically bind to CCR8range generally from about 1 ng, more generally from about 10 ng, typically from about 100 ng; more typically from about 1 $\mu$g, more typically from about 10 $\mu$g, preferably from about 100 $\mu$g, and more preferably from about 1 mg per kilogram body weight. Although higher amounts may be more efficacious, the lower doses typically will have fewer adverse effects. Generally, the range will be less than 100 mg, preferably less than about 50 mg, and more preferably less than about 25 mg per kilogram body weight.

Other antagonists of the ligands, e.g., muteins, are also contemplated. Hourly dose ranges for muteins range from at least about 10 $\mu$g, generally at least about 50 $\mu$g, typically at least about 100 mg, and preferably at least 500 mg per hour. Generally the dosage will be less than about 100 mg, typically less than about 30 mg, preferably less than about 10 mg, and more preferably less than about 6 mg per hour. General ranges will be from at least about 1 $\mu$g to about 1000 $\mu$g, preferably about 10 $\mu$g to about 500 $\mu$g per hour.

The phrase "effective amount" means an amount sufficient to modulate or ameliorate a symptom, or time of onset of symptom, typically by at least about 10%; usually by at least about 20%, preferably at least about 30%, or more preferably at least about 50%. Typical mammalian hosts will include mice, rats, cats, dogs, and primates, including humans. An effective amount for a particular patient may vary depending on factors such as the condition being treated, the overall health of the patient, the method, route, and dose of administration and the severity of side effects. When in combination, an effective amount is in ratio to a combination of components and the effect is not limited to individual components alone.

Administration of the CCR8reagents of the present invention may be in association with: an anti-inflammatory agent; a cytokine agonist or antagonist including especially an antagonist of a Th2 cytokine such as IL-5, IL-13 or IL-4; an analgesic; a steroid; or an anti-allergic agent. Administration regimens for the various combination therapies provided by this invention are known in the art and can be found, for example, in Coffinan et al., 1989, *Science*, 245: 308–310 and U.S. Pat. No. 5,096,704 (IL-5 antagonists); WO/05183, U.S. Pat. No. 5,914,110 and WO89/06975 (IL-4 antagonists).

The present invention provides reagents which will find use in additional diagnostic and therapeutic applications as described elsewhere herein, e.g., in the general description for physiological or developmental abnormalities, or below in the description of kits for diagnosis. See, e.g., Berkow (ed.) *The Merck Manual of Diagnosis and Therapy*, Merck & Co., Rahway, N.J.; Thorn, et al. *Harrison's Principles of Internal Medicine* McGraw-Hill, N.Y.; Gilman, et al. (eds. 1990) *Goodman and Gilman's: The Pharmacological Bases of Therapeutics* 8th Ed., Pergamon Press; (1990) *Remington's Pharmaceutical Sciences* (18th ed.) Mack Publishing Co., Easton, Penn; Langer (1990) *Science* 249:1527–1533; *Merck Index*, Merck & Co., Rahway, N.J.; Avis, et al. (eds. 1993) *Pharmaceutical Dosage Forms: Parenteral Medications* 2d ed., Dekker, N.Y.; Lieberman, et al. (eds. 1990) *Pharmaceutical Dosage Forms: Tablets* 2d ed., Dekker, N.Y.; Lieberman, et al. (eds. 1990) *Pharmaceutical Dosage Forms: Disperse Systems* Dekker, N.Y.; Fodor, et al. (1991) *Science* 251:767–773, Coligan *Current Protocols in Immunology*; Hood, et al. *Immunology* Benjamin/Cummings; Paul (ed.) *Fundamental Immunology; Methods in Enzymology* Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography*, Academic Press, New York; each of which is incorporated herein by reference. Additional uses will be apparent to a person having ordinary skill in the art in light of the teachings provided herein.

IX. Kits

This invention also contemplates use of CCR8and its ligands, fragments thereof, peptides, and their fusion products and related reagents in a variety of diagnostic kits and methods for detecting the presence of a binding composition as described in, e.g., Harlow and Lane (1988) *Antibodies: A Laboratory Manual* CSH; U.S. Pat. Nos. 3,645,090; 3,940,475; Rattle, et al. (1984) *Clin. Chem.* 30:1457–1461; U.S. Pat. No. 4,659,678; and Viallet, et al. (1989) *Progress in Growth Factor Res.* 1:89–97; each of which is incorporated herein by reference.

The broad scope of this invention is best understood with reference to the following examples, which are not intended to limit the invention to specific embodiments.

EXAMPLE I

General Methods

Some of the standard methods are described or referenced, e.g., in Maniatis, et al. (1982) *Molecular Cloning: A Laboratory Manual* Cold Spring Harbor Laboratory, Cold Spring Harbor Press; Sambrook, et al. (1989) *Molecular Cloning: A Laboratory Manual* (2d ed.) vols. 1–3, CSH Press, NY; Ausubel, et al. (1987 and Supplements) *Current Protocols in Molecular Biology*, Greene/Wiley, New York; or Innis, et al. (eds. 1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Coligan, et al. (eds. 1995 and periodic supplements) *Current Protocols in Protein Science* Wiley & Sons; Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry*, Liss, New York, N.Y.; and Robinson, et al. (1993) *Handbook of Flow Cytometry Methods* Wiley-Liss, New York, N.Y.

All cytokines and chemokines used in these studies were obtained as purified carrier-free recombinant proteins from PeproTech Inc., Rocky Hill, N.J. and R&D Systems, Minneapolis, Minn. Interleukins 2, 4, 5, 13 and IFN-γ were measured by standard ELISA using commercially available reagents (R&D Systems, Minneapolis, Minn. and Pharmingen, San Diego, Calif.); sensitivities ranged from 15 to 50 pg/ml.

Cytokine primers and probes (18–22mer) were designed based upon MRNA nucleotide sequences downloaded from the NCBI database and using primer design software (Premier Biosoft International, Palo Alto, Calif.).

All primers and biotinylated probes were prepared by Genosys Biotechnologies Inc., The Woodlands, Tex.

All isolated RNA was reverse transcribed (RT) to DNA by reverse transcriptase polymerase chain reaction (RT-PCR) as follows. To 20 $\mu$g of RNA (in 25 $\mu$l of RNAase-free water) was added 3.6 $\mu$l of RNAsin (Boehringer) and 10 $\mu$l of random hexamer solution (500mg/ml, Promega, Madison, Wis.), followed by heating to 70° C. for 5 min in a thermocycler (Perkin Elmer 9600, Perkin-Elmer Corp, Norwalk, Conn.). The temperature was then reduced to 43° C., then 69 $\mu$l of a first strand buffer (GIBCO BRL, Grand Island, N.Y.) containing dTT, dNTPs and 1000U MMLV reverse transcriptase was added Krug et al., 1987, *Methods Enzymol* 152:316–325. The mixture was incubated for 2 hrs, and then the reaction was stopped by heating to 70° C. The DNA was then subjected to polymerase chain reaction (PCR) according to the method in Saiki et al., 1988, *Science* 24:487–491. Briefly, 5 $\mu$l of DNA was added to 95 $\mu$l PCR buffer containing unlabeled dNTPs (0.2mM of each) plus digoxigenin-labeled dUTP, 1 $\mu$g sense primer, 1 $\mu$g antisense primer and 5 units Taq polymerase (all from Boehringer) in a thin-walled PCR tube. Amplification was then performed in a thermocycler as follows: 4 min at 95° C. followed by 25 cycles of 1 min at 95° C., 2 min at 57° C. and 1 min at 72° C. After cycling there was a DNA extension period of 6 min at 72° C. then samples were stored at −20° C. prior to analysis.

Detection of PCR products was performed by semiquantitative colorimetric PCR-ELISA as previously described in Chensue et al., 1997, *J. Immunol* 159:3565–3573; Hall et al., 1998, *Biotechniques* 24:652–658; Venturoli et al, 1998, *J Clin. Pathol* 51:143–148. A 96-well plate ELISA reader was used to measure O.D. at 405nm at 15 and 30 min. The MRNA ratio was calculated as follows: MRNA ratio=O.D. target gene/O.D. housekeeping gene (cyclophilin). Unlike simple gel detection, the PCR-ELISA method employs a hybridization step that specifically captures target amplicons. Consequently, it is highly specific and has proven to be 10–100 fold more sensitive than gel detection and allows amplification cycles to be kept to a minimum.

The paired Students t-test was used to compare paired groups. Analysis of variance (ANOVA) was used for multigroup analysis. Values of $p>0.05$ were considered to indicate lack of significance.

EXAMPLE II

Gene Targeting

Genomic clones containing murine CCR8were obtained as described in Zingoni et al., 1998, *J Immunol.* 161:547–551. The open reading frame (ORF) of the human CCR8gene was used as a probe to screen the murine 129/SV genomic library in the 1/fix vector (Stratagene, La Jolla, Calif.). Phages were plated and hybridized with the labeled human CCR8cDNA, and positive genomic phage clones were isolated, subcloned, and sequenced as described in Napolitano et al., 1996, *J Immunol.* 157:2759.

A 1.2 kb Bgl II DNA fragment of the mCCR8gene containing the 5' region of homology, and a 6.5 kb Bgl II-Hind Ill fragment containing the 3' region of homology were sequentially cloned into a targeting vector according to the method of Joyner, Gene Targeting; A Practical Approach (Oxford University Press 1993). This targeting vector was designed so that the entire coding sequences of the murine CCR8gene would be replaced with the neoniycin (neo) gene. This DNA was linearized with Not I restriction digestion and electroporated into embryonic stem (ES) cells. Neomycin-resistant ES cell clones were screened for homologous recombination by PCR with the following primers:

TY118 (5'-CACGCTGTTCCATTGCTCTGGAG-3') (SEQ ID NO: 1); and

TY70 (5'-GGGTTTGCTCGACATTGGGTGG-3') (SEQ ID NO: 2).

Five positive clones were identified. Confirmation of the targeted ES cells was done by Southern blot analysis of Pst I digested genomic DNA hybridized to a 0.5 kb 5'-end probe, which detected 2.5 kb and 1.9 kb fragments corresponding to the wild type and mutant alleles, respectively.

Standard PCR techniques can be used to amplify a CCR8gene sequence from genomic DNA or a CCR8fragment from cDNA derived from mRNA. Appropriate primers are selected from the sequences described, and a full-length clone is isolated. Various combinations of primers, of various lengths and possibly with differences in sequence, may be prepared. The full-length clone can be used as a hybridization probe to screen for other homologous genes using stringent or less stringent hybridization conditions.

In another method, oligonucleotides can be used to screen a library. In combination with polymerase chain reaction (PCR) techniques, synthetic oligonucleotides in appropriate orientations are used as primers to select correct clones from a library.

EXAMPLE III

Preparation of a CCR8Deletion Mouse

To make CCR8knockout (KO) mice, four CCR8targeted clones were injected into C57B1/6J blastocysts as described in *Manipulating the Mouse Embryo: A Laboratory Manual*, (1$^{st}$ and 2$^{nd}$ editions, Cold Spring Harbor Laboratory Press, Cold Spring Harbor, N.Y., 1986, 1994). Chimeras from these clones were mated with C57B1/6J females. Germline transmission of the targeted CCR8allele was detected in animals generated from 3 independent clones. Heterozygous mice were bred and CCR8+/+, +/− and −/− genotypes identified. Wild type control B6 X 129 F1 mice were obtained from Jackson Laboratories, Bar Harbor ME. *S. mansoni*-infected Swiss outbred were obtained from Biomedical Research Laboratories, Bethesda, Md. All mice were maintained under specific pathogen-free conditions and provided with food and water ad libitum.

EXAMPLE IV

Initial Observations on CCR8−/− (Knockout) Mice

Intercrosses of CCR8heterozygous (+/−) mice yielded CCR8homozygous null (−/−), (+/−) and wild type (+/+) offspring in the expected Mendelian ratio. RT PCR analysis revealed that CCR8mRNA was present in thymi of control CCR8+/+ mice, but not in those of CCR8−/− mice. This result demonstrates that the CCR8−/− mice are functionally, as well as genetically, null. No obvious abnormalities were seen in the CCR8−/− mice; they developed normally, were fertile, and did not develop spontaneous disease. Histological analysis of all major organs, including lymphoid and hematopoietic organs (thymus, lymph nodes, spleen, blood and bone marrow) failed to reveal significant differences between CCR8−/− and control mice. To determine whether CCR8was required for development of any hematopoietic cell lineage, lymphoid organs were examined by flow cytometry using antibodies directed against a variety of conventional markers: CD3, CD4, CD8, B220, Gr-1, Mac-1, F4/80, CD103, CD11c, Pan-NK, CD44 and TCRγδ. These analyses did not reveal significant differences between CCR8+/+ and −/− mice (n=5). Together, these data demonstrate that the immune system in the CCR8−/− mice is essentially intact.

EXAMPLE V

Primary Response to *Schistosoma mansoni* Eggs

To determine whether CCR8is specifically required for a Th2 immune response, a series of experiments using ova from the helminth parasite, S. mansoni, were performed.

Primary schistosome egg granulomas were induced in lungs by direct tail vein injection of 3000 *S. mansoni* eggs. Study parameters were evaluated at 4, 7, and 14 days post challenge. For comparison of types 1 and 2 granulomas, secondary Ag-bead granulomas were generated as described in Chensue et al., 1997, *J Immunol* 159:3565–3573. Briefly, mice were sensitized by s.c. injection of either 20 μg purified protein derivative (PPD) (Department of Agriculture, Veterinary Division, Ames, Iowa) of M bovis incorporated in to 0.25 ml complete Freund's adjuvant (CFA) (Sigma, St. Louis, Mo., product number F-5881) or 3000 *S. mansoni* eggs suspended in 0.5 ml PBS. Fourteen to 16 days later, PPD or schistosome egg sensitized mice were challenged by tail vein injection of 6000 Sepharose 4B beads (in 0.5 ml PBS) covalently coupled to PPD or to soluble schistosome egg antigens (SEA) (3 ng/bead) obtained from the World Health Organization, Geneva Switzerland.

Lung aqueous extracts from the challenged mice were prepared as follows. Snap frozen lung lobes were suspended in 2ml of PBS and homogenized for 20 seconds using a Tissue Tearor (Biospec Products, Inc. Bartlesville, Okla.). Fetal bovine serum (0.1 ml) was added as a protein stabilizer. The homogenate was centrifuged at 3000 g for 20 min then the supernate was collected, aliquoted, and frozen at −80° C. before cytokine assay. Total protein concentration was determined in experimental and control samples, then cytokine levels were normalized to mg lung protein after subtraction of the FBS protein component.

Lungs and draining lymph nodes were excised and prepared as described below. In some experiments, lungs were inflated and fixed with 10% buffered formalin for morphometric analysis. Granuloma area was measured in a blinded fashion in hematoxylin- and eosin-stained sections of paraffin-embedded lungs using a morphometer and software program (The Morphometer, Woodshole, Mass.). A minimum of 20 lesions was measured per lung. Only granulomas with full cross-sections of the bead nidus were measured.

To perform differential analyses of granulomas, blood, and bone marrow, dispersed granulomas were prepared as described in Chensue et al., 1995, *J Immunol* 154:5969–5976. A 200-cell differential analysis was performed on duplicate Wright stained cytospin preparations of dispersed granulomas. At the time of sacrifice, samples of blood were obtained for total leukocyte counting and 100-cell differential. Bone marrow was obtained by perfusion of the femur then cytospin preparations were subjected to 200-cell differential.

Intravenous challenge of wild type mice with these ova results in pulmonary granulomas at the site of egg deposition. Initially, these granulomas are associated with an IFN-γ mediated mononuclear cell response. However, after 14 to 20 days, the lesions evolve into a vigorous Th2-dominated response, in which eosinophil recruitment is a major component. During this time, the draining lymphoid tissues likewise shift to a Th2-dominant cytokine profile [Chensue et al., 1994, *Clin. Exp. Immunol* 98:395–400].

Several differences were apparent between CCR8−/− mice and control CCR8+/+ mice upon challenge with *S. mansoni* ova. Compared to challenged control mice, the mean granuloma area in challenged CCR8−/− mice at day 14 was reduced by 50% (p<0.005). These lesions also tended to contain a lower proportion of eosinophils although this difference did not achieve statistical significance.

To determine the cytokine profile of draining lymph nodes, they were harvested from challenged mice and lymphocyte cultures derived from them. Mediastinal lymph nodes were collected aseptically at the time of lung harvest and teased into a single cell suspension. After washing, the cells were cultured at $5\times10^6$ cells/ml in RPMI-1640 medium (JRH Biosciences, Lenexa, Kans.) containing 10% FBS (Intergen, Purchase, N.Y.), 10 mM glutamine, and 100 μg/ml streptomycin and 100 U/ml penicillin (RPMI-FBS) in 100 mm dishes with 5 μg/ml PPD or SEA. After 24 hr incubation at 37 C in a humidified 5% $CO_2$ atmosphere, supernates were collected by centrifugation and stored at −45° C. before performing cytokine assays.

Lymphocytes from challenged CCR8+/+ mice displayed the cytokine pattern typical of an evolving Th2 response to *S. mansoni* eggs [Chensue et al., 1994, *J. Clin. Pathol* 51:143–148]. Cells harvested at day 4 post-challenge produced IFN-γ, IL-2 and IL-13, whereas cells harvested at day 14 had lower levels of IFN-γ and IL-2, but increased levels of the Th2 cytokines IL-5 and IL-13. The cytokine profile of lymphocytes harvested from CCR8−/− mice at day 4 did not differ significantly from that of control mice harvested at the same time. However, lymphocytes harvested at day 14 from CCR8−/− mice had markedly reduced levels of IL-5 and IL-13 compared to cells taken from challenged control CCR8+/+ mice at day 14. Thus, later during the Th2 response, the CCR8−/− mice had a blunted Th2 cytokine profile. Interestingly, levels of IL-4 remained below 100 pg/ml in cultures derived from both CCR8−/− and control mice. This reproducible result indicates that in this assay, IL-4 is not a dominant cytokine in mice having the mixed genetic background derived from the C57BL/6 and 129 strains.

EXAMPLE VI

Memory Th2 Response

This example demonstrates that CCR8 is required for a memory Th2 response.

Th2 memory responses can be studied in mice by sensitizing them with a subcutaneous injection of *S. mansoni* eggs, followed two weeks later by an intravenous challenge of agarose beads covalently coupled to schistosomal egg antigen (SEA). In this model, the antigen-coated beads embolize to the lung where they induce a type-2 granulomatous response that is maximal at day 4 [Chensue et al., 1994, Am. J. Pathol 145:1105–1113; Chensue et al., 1995, J. Immunol 154:5969–5976]. To determine whether CCR8 was expressed in this Th2 memory response, mRNA was prepared from granulomas of control mice. CCR8 message was readily seen, suggesting that this receptor might have a role in this Th2 type memory. CCR8−/− and control CCR8+/+ mice were therefore sensitized and challenged as described above, and granulomas harvested at day 4. There were no significant differences in the cross sectional area of lesions between CCR8−/− and control CCR8+/+ mice. However, histologic analysis of granuloma sections of CCR8−/− mice revealed that they had fewer eosinophils than lesions of control mice. Quantitative cellular analysis following enzymatic dispersal of lesions confirmed that the CCR8−/− mice had a 50% decrease in eosinophils compared to control mice. Interestingly, a corresponding 50% increase was seen in the number of macrophages present in the CCR8−/− lesions.

Analysis of granuloma MRNA revealed that compared to control mice, levels of IL-5 and IL-13 in CCR8−/− mice were reduced by approximately 30% and 40%, respectively. IL-4 transcript levels were unchanged, whereas IFN-γ transcripts were increased 2 to 3-fold in the CCR8−/− mice. A determination of protein levels by ELISA confirmed most of these changes; there was a significant reduction in IL-5, a more dramatic reduction in IL-13, and no detectable change in IL-4 in the lungs of CCR8−/− mice. Interestingly, the levels of IFN-γ protein were unchanged despite the observed increase in the message encoding it.

To determine if the reduced levels of Th2 cytokines seen in the granulomas of CCR8−/− mice also extended to lymphoid tissue, draining mediastinal lymph nodes were cultured and analyzed for cytokine profiles. Again, levels of IL-5 and IL-13 in the CCR8−/− derived cells were significantly lower than in cells from control mice, with IL-13 showing a dramatic reduction. In addition, the normally low IFN-γ levels in type-2 cultures were increased by nearly ten-fold in the CCR8−/− cells by comparison to control cells. IL-4 levels in both control and CCR8−/− cultures remained below 150 pg/ml and changes could not be clearly established.

EXAMPLE VII

Th1-Mediated Responses of CCR8−/− Mice

To determine whether the reduction in Th2-type cytokines seen in CCR8−/− mice was restricted to the Th2 response or whether these changes reflected a more general immune defect, we studied responses to an antigen that elicits a Th1 type response. Mice were sensitized subcutaneously with M. bovis PPD in Freund's complete adjuvant, then challenged two weeks later with agarose beads covalently coupled to PPD. Like SEA-coupled beads, PPD-coupled beads embolize to the lung where they induce granuloma formation lung 4 days post-challenge, but these PPD-induced granulomas are characteristic of Th1 cells.

No difference between CCR8−/− and control CCR8+/+ mice were seen in cross-sectional area of the PPD-induced granulomas, and the lesions were histologically indistinguishable by both histological and cellular analyses. Similarly, no marked differences were seen in the levels of interferon-γ, IL-4, IL-5 or IL-13 at either the mRNA or protein level. In addition, both groups of challenged mice had marked increases in IFN-γ message compared to unchallenged mice. In the CCR8−/− mice, there was a trend to even lower IL-5 and IL-13 levels compared to control CCR8+/+ mice. Analysis of cytokine production by lymphocytes harvested from draining lymph nodes revealed that both groups had high levels of IFN-γ production and low levels of IL-5 and IL-1 3, although the levels of the latter two cytokines were even lower in cells derived from the CCR8−/− mice.

EXAMPLE VIII

Eosinophil Production is Impaired in CCR8−/− Mice

To determine whether the reduced number of eosinophils in Th2 type granulomas in CCR8−/− mice was associated with reduced numbers of these cells in the blood and bone marrow, the eosinophil content of these tissues was analyzed.

Eosinophils were obtained from either the spleen or blood of transgenic mice expressing the IL-5 gene in multiple tissues (L. Sullivan and S.A.L., manuscript in preparation). After lysing red blood cells in lysis buffer (Sigma), cells were spun and the pellets resuspended in RPMI supplemented with 10% fetal calf sera and 50 μM 2-mercaptoethanol. Cells were cultured for 5 days and used for RNA and Ca$^{++}$ flux experiments. Prior to RNA extraction, the viability and cellular composition was examined by flow cytometry and H&E staining. Over 90% of the cells in culture were alive, had typical cytoplasmic eosinophilic granules and were CCR3/Mac-1 positive. RNA was extracted by conventional methods from the thymus of both CCR8+/+ and −/− mice (as control for CCR8reaction) and from the cultured eosinophils using methods described below. cDNA was synthesized using SuperScript Preamplification System (GIBCOBRL) according to manufacturer's recommendations.

The PCR conditions were as follows: 94° C. for 2 min, then 35 cycles of 94° C. for 3 min, 55° C. for 1 min, 72° C. for 1 min and 72° C. for 5 min. The final PCR products were analyzed on a 2% agarose gel containing ethidium bromide. Calcium flux was examined in real time using fluorescence imaging plate reader (FLIPR; Molecular Devices, Sunnyvale, Calif.). Eosinophils were loaded with Fluo-3-AM (Sigma Chemical, St. Louis, Mo.) in RPMI containing 10% serum for 1 h at 37° C. after which cells were washed 3 times in flux buffer (Hank's balanced salt solution, 20 mM HEPES, 0.1BSA) and aliquoted into a 96-well black-walled plates at a density of $5 \times 10^5$ cells/well. All plates were pre-coated with poly-L-lysine. The data obtained were expressed as fluorescence units versus time. Chemokines were obtained from R&D Systems (Minneapolis, Minn.).

For lung RNA extraction, perfused lung lobes excluding major bronchi were snap frozen with liquid nitrogen and total cellular RNA was extracted by a method similar to that described in Chirgwin et al., 1979, Biochem 18:5294–5299 and Jonas et al., 1985, Proc. Natl. Acad. Sci. USA 82:5413–5417. Specifically, the frozen tissues were suspended in extraction buffer (25 mM Tris pH 8.0, 4.2M guanidine isothiocyanate, 0.5% Sarkosyl and 0.1M 2-mercaptoethanol), homogenized, then added to an equal volume of extraction buffer (100 mM Tris, pH 8.0, 10mM EDTA and 1% SDS). The mixture was then serially extracted with chloroform-phenol and chloroforn-isoamyl alcohol. The RNA is next precipitated at −70° C. in ethyl alcohol, washed and reprecipitated. The pellet was finally dissolved in DEPC water and RNA concentrations determined spectrophotometrically prior to storage at −70° C. Yields are routinely greater that 100 μg.

No differences between CCR8−/− and control CCR8+/+ mice were seen in blood leukocyte populations during the type-1 response. However, during the type 2 response, CCR8−/− mice had a 70% decrease in absolute numbers of circulating eosinophils. The CCR8−/− mice also had reduced eosinophil differentiation in bone marrow, with the ratio of eosinophil to neutrophil differentiation decreasing by 50%.

IL-5 is an important mediator of eosinophil differentiation in bone marrow Yamaguchi et al., 1988, J Exp. Med. 167:43–56 and it is required for eosinophil recruitment to schistosome egg-induced granulomas [Sher et al, 1990, Proc. Natl. Acad. Sci. USA 87:61–65]. To determine whether the reduced eosinophilic content of the blood and marrow was associated with a reduction in systemic IL-5 release, we measured serum IL-5 levels in mice with ongoing type-2 immune responses. This analysis revealed that IL-5 was significantly reduced in serum.

EXAMPLE IX

Circulating Eosinophils Do not Express CCR8Nor Respond to CCR8Ligands

One possibility for the reduced numbers of eosinophils in granulomas of CCR8−/− mice was that CCR8is expressed by eosinophils and directly mediates recruitment of these cells to the lesions. To test this possibility, CCR8expression and signaling (calcium flux and chemotaxis) in mouse eosinophils having an intact CCR8gene were examined. No CCR8mRNA was detected in these cells by RT PCR, although expression of the eosinophil-associated chemokine receptor CCR3 was readily detected under similar conditions. In addition, the CCR8ligands TCA-3 and its human homologue I-309 both failed to induce calcium flux in eosinophils, whereas a robust response was obtained with the CCR3 ligand, eotaxin. In vitro chemotaxis assays gave similar results using both blood- and spleen-derived eosinophils.

EXAMPLE X

Induction of a Th2 Type Response With Cockroach Allergen

In order to induce a Th2 type response, the following procedures were established in normal C57/BL6 mice. The mice were immunized with 1 0 μg of cockroach allergen (Bayer 10 Pharmaceuticals,) in incomplete Freunds adjuvant (IFA) on day 0. On day 14 the mice were given an intranasal challenge of 10 μg of cockroach allergen in 10 μl of diluent to localize the response to the airway. This initial intranasal challenge with antigen induces little cellular infiltrate into the lungs of the mice upon histological examination. Mice were then rechallenged six days later by intratracheal administration of 10 μg of cockroach allergen in 50 μl of sterile PBS or with PBS alone (vehicle). The magnitude of leukocyte recruitment in both the vehicle control and cockroach allergen challenged mice were examined histologically. Only the cockroach allergen-challenged mice displayed a significant inflammatory response which includes mononuclear cell and eosinophil infiltration. For secondary rechallenge, the mice again were given an intratracheal injection of either cockroach allergen (10 μg in 50 μl) or diluent control and subsequently analyzed.

Mice immunized and challenged with cockroach allergen were euthanized and the lungs removed, collagenase (0.2% Sigma Type IV) treated, and dispersed into single cell suspensions. The cells were then counted and total leukocyte numbers determined for each mouse. The single cell suspensions were then cytospin fixed and a percentage of leukocyte subsets were determined by examination of 200 leukocytes. The percentage of lymphocyte populations were determined by flow cytometry.

Flow cytometric analysis of lymphocyte subsets were carried out in dispersed lung samples from normal and CCR8−/− allergic mice. The staining procedure was performed on ice in Dulbecco's phosphate buffered saline (D-PBS) with 2% FBS and 0.1% sodium azide. 1×106 total cells were stained in 100 ul of buffer. Pelleted cells (5 min, 1400 rpm) were incubated for 30 min. on ice with specific antibody, anti-CD4, anti-CD8, or a subclass control (Pharmingen), directly conjugated with FITC. After incubation, an additional 2 ml of cold D-PBS specific antibody was added and the cells pelleted by centrifugation (5 min at 1400 rpm; 4° C.). The pelleted cells were washed twice with D-PBS and resuspended in 100 μl of 1% paraformaldehyde for 15 min. After incubation, the cells were centrifuged with the addition of 2 ml of D-PBS and stored at 4° C. in D-PBS containing 0.1% sodium azide until analyzed by flow cytometry. Cells were analyzed within 24 hrs of staining procedure.

Lungs from allergic control and CCR8−/− mice were dispersed and leukocyte subset numbers were determined. Table I shows the T lymphocyte numbers in CCR8−/− mice.

TABLE 1

CCR8 −/− mice have no alteration in lymphocyte subset numbers during allergen-induced responses in dispersed lung tissue.

| Group | Macs | Lymphs | CD4 | CD8 | eosinophils | total cell number |
|---|---|---|---|---|---|---|
| Control | 25% | 34 | 18.5% | 10.3% | 27% | 2.6 × 10⁷ |
| CCR8 −/− | 46% | 35 | 16.8% | 12.4% | 14% | 2.4 × 10⁷ |

*Data is representative of 3 repeat experiments.

There was an increase in the number of mononuclear phagocytes and a significant reduction in granulocyte numbers (eosinophils) Eosinophil penoxidase (EPO) levels were also reduced in the BAL fluid of the CCR8−/− mice.

EXAMPLE XI

Eosinophil Levels in Cockroach Allergen Challenged CCR8−/− Mice

To determine if the reduced numbers of cosinophils in the lung were consequence of reduced recruitment into the lung parenchyma or reduced production by the bone marrow, the number of circulating eosinophils was measured. Blood smears from littermate control or CCR8−/− were differentially stained using Diff Quik (Dade Behring, Newark, Del.) solution and the % and total number of eosinophils /ml of blood was analyzed by microscopic examination.

There was no difference in the numbers of eosinophils between non challenged +/+ and −/− CCR8mice. In contrast, there was a significant reduction in the number of circulating eosinophils in the antigen-challenged mice. Eosinophils averaged 10.3±3.7% of the circulating cells in the +/+ group and less than <2%, in the CCR8−/− mice. These results suggested a deficit in eosinophil maturation and release into circulation.

EXAMPLE XII

Cytokine Levels in Cockroach Allergen Challenged CCR8−/− Mice

IL-5 levels were examined in the lungs of allergic mice. Cytokines were analyzed in the lungs by preparing whole lung homogenates in a PBS buffer containing anti-proteases and 0.1% Triton X-100 nonionic detergent. Cell-free supernatants were prepared by subjecting the homogenates to high-speed centrifugation (10,000×g) for 10 minutes. The supernatants were then assayed by specific ELISA for IL-5 (R & D Systems, Rochester, Minn.). A significant decrease in the IL-5 levels were observed, correlating directly with the deficit of circulating and accumulated eosinophils in the CCR8−/− mice.

Because CCR8has been described to be expressed predominantly on Th2 type lymphocytes in vitro, the cytokine levels within the lung were assessed using whole lung homogenates at different time points during the response. Cytokine levels were measured in whole lung homogenates using specific antibody pairs (R & D Systems) for sandwich ELISAs. The sensitivity of the analysis was ~10 pg/ml. IL-13 ELISA was prepared using polyclonal antiibodies made in our laboratory [Chensue et al., 1999, *J Immunol.* 163(1):165–73]. The levels of IFN-γ, IL-10, and IL-12 were not altered within the CCR8−/− compared to the littermate control lungs. However, the levels of pulmonary IL-4 and IL-13 were significantly reduced in the CCR8−/− compared to the littermate control mice during the developing stages of disease after an allergen challenge. Interestingly, IL-4 levels were reduced early, whereas IL-13 levels were significantly altered during the latter stages of the disease. These findings, along with the IL-5 data above, indicate a defective Th2 response in these animals.

EXAMPLE XIII

Levels of IgE in Cockroach Allergen Challenged CCR8−/− Mice

To test if the levels of IgE are altered in the CCR8deficient mice, serum from chronically sensitized and challenged littermate control or CCR8−/− mice was isolated and the level of total IgE was measured. IgE was measured in individual serum samples collected from normal or allergic mice. The assay used was a sandwich ELISA specific for mouse IgE and measured total serum IgE (Pharmingen, San Diego, Calif.). The CCR8−/− mice demonstrated a significant decrease in total circulating levels of IgE. These results indicate that deletion of CCR8may drastically alter the sensitization process in this model and suggest that CCR8deletion may negatively influence the overall Th2 type response.

EXAMPLE XIV

Levels of Eosinophil Associated Chemokines in Cockroach Allergen Challenged CCR8−/− Mice Several eosinophil associated chemokines, including C10, eotaxin, RANTES, MIP-1alpha, and MCP-3 were measured. Assessment of chemokines were quantitated from homogenized (PBS) lung aqueous extracts or cell-free supernatants from dispersed cultured cells using a double ligand ELISA system. The murine ELISAs have been developed in our laboratories using a previously described method [Evanoff et al., 1992, *Immunol. Invest.* 21:39]. ELISAs were conducted as follows: Flat bottomed 96 well microtiter plates (Nunc Immuno-Plate I 96° F.) were coated with capture antibody diluted to 3.2 ug/ml in coating buffer (borate-buffered saline, ph 8.6) and incubated overnight at 4° C. Nonspecific binding sites were blocked with 2% BSA in PBS and incubated for 1 hour at 37° C. Plates were washed and specimens added in triplicate followed by incubation at 37° and washing. Biotinylated detection antibody was added and the plates incubated at 37° C. for 1 hr. Plates were washed and conjugated streptavidin-peroxidase was added, followed by washing and the addition of chromogen substrate (OPD). Finally plates were incubated at room temperature, the reaction terminated with 3M $H_2SO_4$ and read at 490 nm in an ELISA reader. The individual polypeptides were standardized to total protein (ng/$\mu$g total protein). Our ELISAs routinely detect protein at concentrations above 50 pg/ml. These ELISAs are specific and do not cross react to any other chemokine or cytokine.

The levels of these chemokines within the lung parenchyma were similar between challenged +/+ and −/− mice. The only exception was eotaxin, which was shown to be significantly reduced in the CCR8−/− mice.

EXAMPLE XV

Changes in Airway Physiology in Cockroach Allergen Challenged CCR8−/− Mice

This Example demonstrates that CCR8is important in the development of airway hyperreactivity after chronic allergen challenges.

Airway hyperreactivity was measured using a Buxco mouse plethysmograph which is specifically designed for the low tidal volumes (Buxco, Troy, N.Y.). Briefly, the mouse to be tested was anesthetized with sodium pentobarbital and intubated via cannulation of the trachea with an 18 gauge metal tube. The mouse was subsequently ventilated with a Harvard pump ventilator (tidal volume=0.4 ml, frequency=120 breaths/min, positive end-expiratory pressure 2.5–3.0 cm H2O) and the tail vein was cannulated with a 27 g needle for injection of the methacholine challenge. The plethysmograph was sealed and readings monitored by computer. Since the box is a closed system, a change in lung volume was represented by a change in box pressure (Pbox) which was measured by a differential transducer. The system was calibrated with a syringe that delivered a known volume of 2 ml. A second transducer was used to measure the pressure swings at the opening of the trachea tube (Paw), referenced to the body box (i.e. pleural pressure), and to provide a measure of transpulmonary pressure (Ptp=Paw-Pbox). The trachea transducer was calibrated at a constant pressure of 20 cmH2O. Resistance is calculated by the Buxco software by dividing the change in pressure (Ptp) by the change in flow (F) (_Ptp/_F; units=cmH2O/ml/sec) at two time points from the volume curve based upon a percentage of the inspiratory volume. Once the mouse was hooked up to the box it was ventilated for 5 minutes prior to acquiring readings. Once baseline levels are stabilized and initial readings were taken, a methacholine challenge was given via the cannulated tail vein. After determining a dose response curve (0.001 to 0.5 mg), an optimal dose was chosen, 0.1 mg of methacholine. This dose was used throughout the rest of the experiments in this study. After the methacholine challenge, the response was monitored and the peak airway resistance was recorded as a measure of airway hyperreactivity.

After a single intratracheal allergen challenge, the CCR8−/− mice showed no alteration in airway hyperreactivity. However, the pathophysiological responses associated with severe asthma are associated with multiple exposures, therefore making chronic asthmatic responses most relevant. Therefore, we examined whether deletion of CCR8affected the pathophysiologic responses to methacholine in a more chronic setting. After a second intratracheal allergen challenge, given 48 hours post-primary challenge, the CCR8−/− mice demonstrated a significantly attenuated airway hyperractive response.

EXAMPLE XVI

Induction of a Th2 Type Response with Ovalbumin

Mice were sensitized by an i.p. injection of 0.5 ml of alum-precipitated antigen containing 15 $\mu$g of ovalbumin (OVA) absorbed to 2 mg of aluminum hydroxide (alum) gel in saline vehicle followed 5-days later by a booster injection of this alum-OVA mixture. Non-sensitized control animals received alum gel only. Twelve days after the sensitization, all mice were placed in plexiglas chamber and exposed to aerosolized OVA (0.5%) for 1 hour both in the morning and afternoon of a single day. The aerosolized OVA was produced by an ultrasonic nebulizer (DeVilbiss, Somerset, Pa.; Model Ultra-Neb 99) at a flow rate of approximately 5 l/min. Forty-eight hours after OVA challenge, the mice were sacrificed by CO2 asphyziation. The trachea was exposed and cannulated with a 24 gauge needle. The lungs were then lavaged with 0.3 ml phosphate buffered saline. Approximately 0.2 ml of the instilled fluid was retrieved. Total cell numbers were counted with a standard hemocytometer. Smears of BAL cells were made by cytocentrifuging 100 $\mu$l of BAL fluid (Shannon Inc., Pittsburgh, Pa.) at 150 g for 10 minutes. The smears were fixed and stained with Leukostat stain (Fischer Scientific, Pittsburgh, Pa.). Differential cell counts were determined from at least 200 leukocytes.

EXAMPLE XVII

Histological Analysis of Ovalbumin Challenged Mice

Lung tissues were prepared for histology by flushing the pulmonary artery with 2.5 ml of phosphate buffered saline (pH 7.2) using a 24 gauge needle in situ. The lungs were then removed and fixed with 10% phosphate-buffered formalin for 24 hr. The left lobe was embedded in paraffin, sectioned at 5 µM and stained with hematoxyin and eosin. Enumeration of the peribronchial eosinophils were made at 500× magnification and the average of 5 high powered field determinations were made in each animal.

EXAMPLE XVIII

Preparation of Antibodies Specific for CCR8

Now that the role of CCR8in the in vivo inflammatory response is better understood, antagonists of CCR8, including antibodies, will be extremely useful.

Inbred Balb/c mice are immunized, e.g., with 1 ml of purified CCR8emulsified in Freund's complete adjuvant on day 0, and in Freund's incomplete adjuvant on days 15 and 22. The mice are boosted with 0.5 ml of purified CCR8administered intravenously.

Hybridomas are created, e.g., using the non-secreting myeloma cells line SP2/0-Ag8 and polyethylene glycol 1000 (Sigma, St. Louis, Mo.) as the fusing agent. Hybridoma cells are placed in a 96-well Falcon tissue culture plate (Becton Dickinson, N.J.) and fed with DMEM F12 (Gibco, Gaithersburg, Md.) supplemented with 80 µg/ml gentamycin, 2 mM glutamine, 10% horse serum (Gibco, Gaithersburg, Md.), 1% ADCM (CRTS, Lyon, France) $10^{-5}$ M azaserine (Sigma, St. Louis, Mo.) and $5 \times 10^{-5}$ M hypoxanthine. Hybridoma supernatants are screened for antibody production against CCR8, e.g., by immunocytochemistry (ICC) using acetone fixed CCR8transfected COS-7 cells and/or by ELISA using CCR8purified from COS-7 supernatants as a coating antigen. Aliquots of positive cell clones are expanded for 6 days and cryopreserved as well as propagated in ascites from pristane (2,6,10,14-tetramethylpentadecane, Sigma, St. Louis, Mo.) treated Balb/c mice who had received on intraperitoneal injection of pristane 15 days before. About $10^5$ hybridoma cells in 1 ml of PBS are given intraperitoneally, and 10 days later, ascites are collected from each mouse.

After centrifugation of the ascites, the antibody fraction may be isolated by ammonium sulfate precipitation and anion-exchange chromatography on a Zephyr-D silicium column (IBF Sepracor) equilibrated with 20 mM Tris pH 8.0. Proteins are eluted with a NaCl gradient (ranging from 0 to 1 M NaCl). 2 ml fractions may be collected and tested by ELISA for the presence of anti-CCR8antibody. The fractions containing specific anti-CCR8activity are pooled, dialyzed, and frozen.

EXAMPLE XIX

Drug Screening Methods

The identification of CCR8as a target for asthma therapeutics provides new drug screening methods. Specifically, drug screening using CCR8or variants or fragments thereof can be performed to identify compounds which have binding affinity to CCR8, or which can block the natural interaction with ligand. Subsequent biological assays can then be utilized to determine if the compound has intrinsic blocking activity and is therefore an antagonist.

It is well known in the art how to screen for small molecules which interfere, e.g., with ligand binding to the receptor, often by specific binding to the receptor and blocking of binding by natural ligand. See, e.g., Meetings on High Throughput Screening, International Business Communications, Southborough, Mass. 01772-1749. Such molecules may compete with natural ligands, and selectively bind to the CCR8. Possible screening methods include incubating components comprising a test composition and CCR8under conditions sufficient to allow the components to interact and measuring the binding of the composition to CCR8. Compositions that bind to CCR8include peptides, peptidomimetics, polypeptides, chemical compounds and biologic agents as described above. Incubating includes conditions which allow contact between the test composition and CCR8. Contacting includes in solution and in solid phase. The test ligand(s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saike, et al., 1985, *Bio/Technology*, 3:1008–1012), allele-specific oligonucleotide (ASO) probe analysis (Conner, et al., 1983, *Proc. Natl. Acad. Sci. USA*, 80:278), oligonucleotide ligation assays (OLAs) (Landegren, et al., 1988, *Science*, 241:1077) and the like. Molecular techniques for DNA analysis have been reviewed (Landegren, et al., 1988, *Science*, 242:229–237).

All references cited herein are incorporated herein by reference to the same extent as if each individual publication or patent application was specifically and individually indicated to be incorporated herein by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

---

What is claimed is:

1. A transgenic mouse whose genome comprises a homozygous disruption in the CCR8gene, wherein said mouse exhibits a defective Th2 response when challenged with an allergen as compared to wild-type mice challenged with the allergen, and wherein said defective Th2 response comprises decreased granuloma area, decreased levels of IL-5 production, decreased levels of IL-13 production, and decreased eosinophil recruitment.

2. The transgenic mouse of claim 1, wherein said allergen is selected from the group consisting of Schistosoma mansoni eggs, cockroach allergen, and ovalbumin.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 1
cacgctgttc cattgctctg gag                                            23
```

```
<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 2
gggtttgctc gacattgggt gg                                              22
```